United States Patent [19]

Smith, III et al.

[11] 4,262,623

[45] Apr. 21, 1981

[54] INKLESS FINGERPRINTING DEVICE AND METHOD ADAPTED FOR RECORDATION OF A PLURALITY OF FINGERPRINTS

[75] Inventors: Jay Smith, III, Pacific Palisades; Virgile L. Hedgcoth, Santa Monica; Thomas H. Grimm, Manhatten Beach, all of Calif.

[73] Assignee: Park Management and Development Co., Atherton, Calif.

[21] Appl. No.: 968,361

[22] Filed: Dec. 11, 1978

[51] Int. Cl.³ .............................................. B41K 1/00
[52] U.S. Cl. .................................. 118/31.5; 118/264; 118/265; 118/715; 427/1; 427/145; 427/255.4
[58] Field of Search ............... 118/31.5, 48, 264, 265, 118/715; 427/1, 145, 248 E, 255.4

[56] References Cited

U.S. PATENT DOCUMENTS

| | | | |
|---|---|---|---|
| 2,235,632 | 3/1941 | Heinecke | 427/1 |
| 2,723,476 | 11/1955 | Lyon | 118/264 |
| 3,851,619 | 12/1974 | Cofield | 118/31.5 |
| 3,960,632 | 6/1976 | Gaines et al. | 118/31.5 |
| 4,029,012 | 6/1977 | Smith | 118/31.5 |
| 4,030,934 | 6/1977 | Iijima | 427/145 |

FOREIGN PATENT DOCUMENTS 196425  3/1958  Austria ................................... 118/264

Primary Examiner—Ronald H. Smith
Assistant Examiner—Janyce A. Bell
Attorney, Agent, or Firm—Jackson, Jones & Price

[57] ABSTRACT

A plurality of fingerprints of a person are recorded by applying a solution of a first substantially colorless chemical reagent to the fingertips. Essentially invisible fingerprints are obtained by gently pressing the fingers having the solution of the first chemical reagent thereon on a suitable recording sheet. Subsequently the recording sheet is exposed to sublimed vapors of a second chemical reagent. The first and second chemical reagents are selected to react with one another to yield a highly colored substance which is formed on the surface of the recording sheet providing a visible image of the fingerprints. Ferric chloride and a 8-hydroxyquinoline are ideally suited chemical reagents for use in this invention. An apparatus of unitary construction incorporating a replaceable dispensing pad having the solution of the first chemical, is disclosed. The apparatus also includes a suitable bracket for holding the recording sheet and a chamber wherein the exposure of the latent fingerprint to the sublimed vapors of the second chemical reagent occurs.

19 Claims, 6 Drawing Figures

INKLESS FINGERPRINTING DEVICE AND METHOD ADAPTED FOR RECORDATION OF A PLURALITY OF FINGERPRINTS

BACKGROUND OF THE INVENTION

1. Field of the Invention

The present invention is directed to an improved method and apparatus of fingerprinting, and more particularly to a method and apparatus permitting the inkless recording of fingerprints without any attendant staining of the fingers with ink or highly colored chemicals.

2. Description of the Prior Art

The art of fingerprinting and identifying persons by their fingerprints is well known. The simplest method of taking a person's fingerprints is to apply a highly colored ink or dye to a person's finger tips. Subsequent rolling or pressing of the person's fingers on a clean recording surface, such as paper, deposits the ink or dye on the surface in a pattern corresponding to the fingerprints of the person. While the above simple method has been widely accepted and used by law enforcement agencies and the like, commercial application of fingerprinting has been greatly hampered by the understandable reluctance of people to have their fingers stained by the application of a highly colored ink or dye.

In addition the inherent lubricity of currently used petroleum based inks often causes a relative slipping between the fingers and the ink film. As a result an undesirable smudging or smearing of the fingerprints may occur.

In order to overcome the problem of stained fingers, the prior art has developed a number of methods and devices wherein the risk of having the person's fingers stained by a highly colored chemical or dye is reduced. Such devices, generally termed inkless devices, usually utilize two substantially colorless chemical reagents. The first chemical reagent is applied to the fingers of the person to be fingerprinted. The person then rolls his fingers on a piece of paper or other suitable recording surface, thereby depositing the first chemical reagent in a pattern corresponding to the fingerprint image.

In some prior art devices such as the one disclosed in U.S. Pat. No. 2,299,652, the paper is impregnated with a second chemical reagent. In some other devices such as for example in the one disclosed in U.S. Pat. No. 3,960,632, the paper having the first chemical reagent deposited thereon in a latent fingerprint image is sprayed with the second chemical reagent. The first and second chemical reagents in both instances are selected to react with one another to form a highly colored, preferably dark blue or black substance. The latter develops on the surface of the paper in a pattern corresponding to the fingerprint of the person. Thus, in this manner the fingerprint can be recorded without subjecting the person to the inconvenience of staining his fingers.

The principal requirements for these chemical reagents suitable for inkless fingerprinting are that they be relatively inexpensive, non-toxic, adaptable to storage and are easily applied on the fingers. Furthermore, the rate of the chemical reaction between the reagents should be sufficiently rapid so that the development of the visible fingerprint image can be readily monitored and a determination be made whether a satisfactory image has been obtained. A relatively large number of suitable chemical reagent pairs for this type of application is disclosed in U.S. Pat. No. 2,235,632 as well as in U.S. Pat. No. 4,029,012. U.S. Pat. No. 4,029,012 discloses the use of ferric chloride and 8-hydroxyquinoline solutions in a two-part inkless applicator particularly adapted for quick recording of thumbprints. Additional disclosures relevant to inkless fingerprinting devices can be found in U.S. Pat. No. 3,755,517; U.S. Pat. No. 3,447,818; U.S. Pat. No. 3,851,619 and in British Printed patent specification No. 428,386.

While the prior art inkless fingerprinting devices have solved some of the problems associated with traditional fingerprinting, the prior art inkless devices still generally suffer from the following drawbacks. As a person's finger, having a first chemical reagent thereon, is pressed to a paper surface containing the second chemical reagent, the finger still may be stained by the colored substance which is instantaneously formed as a result of the chemical reaction between the first and second reagents. Spraying the paper sheet with the second chemical having the essentially invisible fingerprint pattern deposited thereon eliminates the above problem. However spraying is a messy procedure and subjects the operator of the fingerprinting device to the risk of possible long term exposure to the second chemical which is freely dispersed by the spray.

It has been suggested in U.S. Pat. No. 2,235,632 that the essentially invisible fingerprint deposited from the person's finger on the paper may be developed by a colorless powder or volatile vapors comprising the second reagent. U.S. Pat. No. 2,235,632 describes a number of substantially colorless chemical reagents or mixtures thereof, which after having been deposited on the surface of the paper may be transformed into a highly colored substance by the application of heat or intense light. However, the application of heat or intense light suffers from the obvious disadvantage that additional appendages to the fingerprinting device such as a heat or a light source may be required. Furthermore, the operator of the fingerprinting device cannot immediately judge whether or not the fingerprint taken is acceptable, since he has to wait until the fingerprint is developed by the application of heat or light.

Developing of the invisible fingerprints by exposure to volatile vapors of the second reagent, as suggested by U.S. Pat. No. 2,235,632, appears to provide certain advantages. However this method has not gained acceptance in the prior art and U.S. Pat. No. 2,235,632 failed to teach specific examples of chemical reagents which are suitable for this type of application in a fingerprinting device. Furthermore most chemical reagents having a sufficiently high vapor pressure at room temperature to enable this type of application comprise gases or volatile liquids. It is readily understood that utilization of a gaseous chemical reagent or of a volatile liquid in a simple, inexpensive and compact fingerprinting device is undesirable. Use of such reagents would not only be impractical but would also increase the risk of exposing the operator of the device to the long term, possibly toxic effects of these chemicals.

For the above stated reasons a need still exists in the prior art for a simple, compact, reliable and inexpensive inkless fingerprinting device. Such a device must not unduly expose its operator to toxic chemicals and must eliminate the possibility of staining a person's fingers with highly colored chemicals.

SUMMARY OF THE INVENTION

It is an object of the present invention to provide a relatively simple, inexpensive and reliable inkless fingerprinting device.

It is another object of the present invention to provide an inkless fingerprinting device which is adapted for the simultaneous recordation of the prints of a plurality of fingers of the same hand of a person.

It is still another object of the present invention to provide an inkless fingerprinting device wherein the possibility of staining a person's fingers with a highly colored chemical substance is eliminated.

It is yet another object of the present invention to provide an inkless fingerprinting method and device wherein the prolonged exposure of an operator of the device to chemical reagents is minimized.

It is a further object of the present invention to provide an inkless fingerprinting device which has a supply of chemical reagents available for a prolonged period of use.

It is still a further object of the present invention to provide an inkless fingerprinting device wherein the supply of chemical reagents, once exhausted, can be readily replenished by discarding a few, inexpensive components of the device and inserting new ones.

It is yet a further object of the present invention to provide an inkless fingerprinting method and device wherein the amount of the chemical reagent to be applied to a person's finger is objectively controlled within acceptable limits.

It is still another object of the present invention to provide an inkless fingerprinting method and device wherein a possibility of relative slipping between the fingers and a film of the applied chemical reagents is eliminated or reduced.

These and other objects and advantages are attained by the following method and device. The fingers of a person are gently rolled or pressed upon the surface of a porous, rigid plate dispensing a solution of a first chemical reagent. The fingerprint patterns are then deposited on a surface of a recording sheet resulting in an essentially invisible fingerprint image. The invisible fingerprint is developed by exposing the recording sheet to a gaseous phase of a second chemical reagent. The second chemical reagent comprises a solid at the operating temperature of the device and has a sufficiently high enough vapor pressure to result in significant sublimation of the second chemical. The first and second chemical reagents react with one another to yield a highly colored reaction product which forms in a pattern corresponding to the fingerprints. Consequently the fingerprints are developed and recorded.

A device having a simple unitary construction embodying the rigid porous plate dispensing the first chemical and a chamber for developing the invisible fingerprint is provided. The second sublimable, solid chemical reagent is best contained finely dispersed within the interstitial spaces of a fibrous or porous resilient pad. The device is also adapted for mechanically securing the recording sheet while the fingerprint is taken, and for bringing the invisible fingerprint into intimate contact with the resilient pad containing the second chemical reagent. Ferric chloride and 8-hydroxyquinoline are utilized as the chemical reagents in the preferred embodiment.

The objects and features of the present invention are set forth with particularity in the appended claims. The present invention may be best understood by reference to the following description taken in connection with the accompanying drawings in which like numerals indicate like parts.

DESCRIPTION OF THE PREFERRED EMBODIMENT

The following specification taken in conjunction with the drawings sets forth the preferred embodiment of the present invention in such a manner that any person skilled in the fingerprinting and chemical arts can use the invention. The embodiment of the invention disclosed herein is the best mode contemplated by the inventors for carrying out their invention in a commercial environment, although it should be understood that various modifications can be accomplished within the parameters of the present invention.

Figure 1:
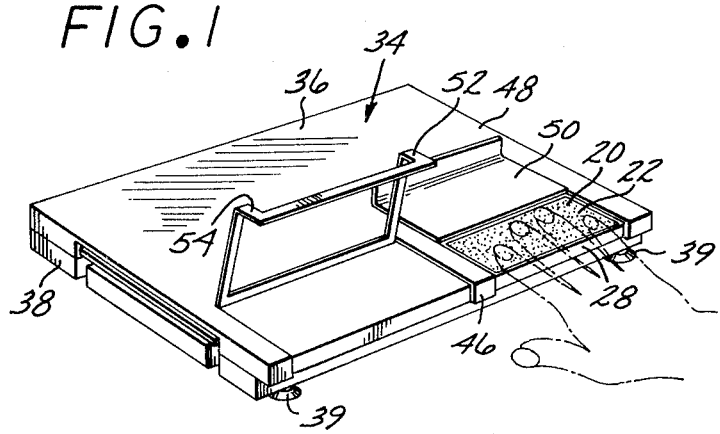
FIG. 1 is a perspective view of a preferred embodiment of the device of the present invention and a representation of a first step of the method of the present invention.
Figure 2:
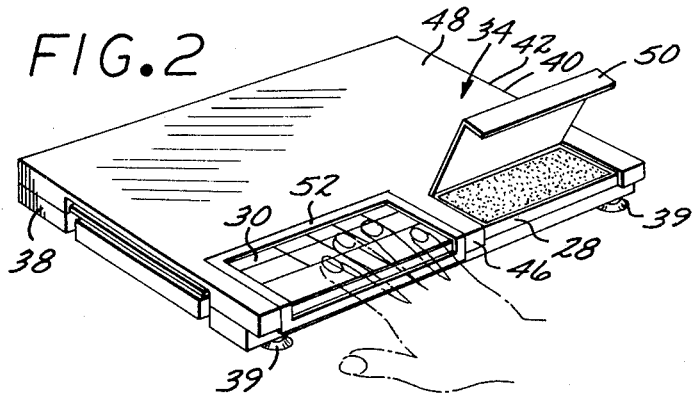
FIG. 2 is another perspective view of the preferred embodiment of the device of the present invention and a representation of a second step of the method of the present invention.
Figure 3:
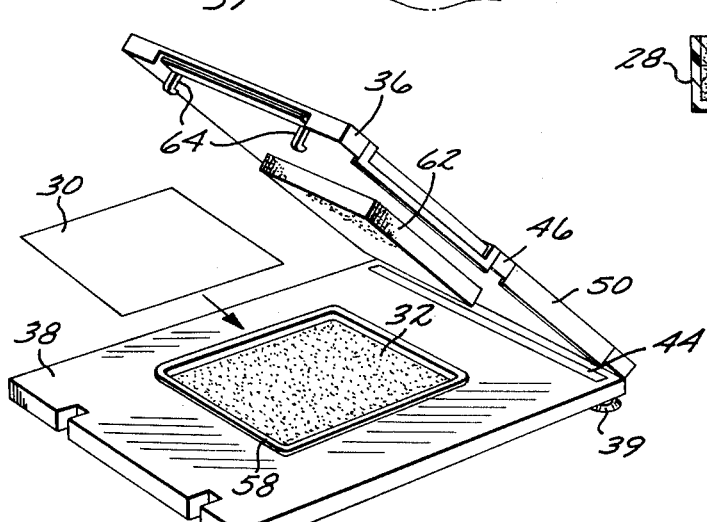
FIG. 3 is yet another perspective view of the preferred embodiment of the device of the present invention and a representation of a third step of the method of the present invention.

Referring to FIGS. 1 through 3 the individual steps of the novel method of inkless recording of fingerprints are disclosed. In a first step, depicted in FIG. 1, the solution of a first chemical reagent is applied to at least one, but preferrably to a plurality of fingers of the person whose fingerprint is to be recorded.

A chemical reagent suitable for such an application must satisfy the following requirements. It must be able to react rapidly with a second chemical to yield a highly colored substance. It must be relatively non-toxic so that a person is not exposed to harmful effects while his fingerprint is taken. Preferrably this first chemical should also be water soluble, and relatively inexpensive.

As it is readily understood by those skilled in the chemical arts, the selection of this first chemical reagent cannot be accomplished independently from the selection of the second chemical reagent. For this reason, a designer in this field is required to select the appropriate chemical reagents in a pair, i.e. suitable and compatible first and second chemical reagents must be chosen. Additional requirements for the selection of the second chemical reagent will be readily understood as the method and apparatus of the present invention is explained below.

In the preferred embodiment of the present invention, ferric chloride, $FeCl_3$ is used as the first chemical reagent. The use of ferric chloride is highly advantageous in view of the fact that it is non-toxic, inexpensive and highly water soluble. Even though ferric chloride gives a colored aqueous solution, it does not stain the fingers to any appreciable extent.

The concentration of the aqueous solution of ferric chloride to be applied to the fingers does not appear to be critical. Good results have been obtained where the concentration of the aqueous ferric chloride solution was within the range of 5-40% by weight, however, an approximately 11% concentration is preferred.

The aqueous solution of ferric chloride which is to be applied to the fingers may contain additional ingredients. For example, addition of glycerol or other water miscible and non-volatile solvents lowers the rate of evaporation of the solution and therefore may improve its utility in this application. However, very satisfactory results have been obtained without the use of glycerol or other solvents.

Furthermore, addition of approximately one to four percent by weight of a surface active agent improves the wetting characteristics of the solution. Therefore inclusion of a surface active agent in the aqueous solution of ferric chloride is advantageous both for physical application to the fingers as well as for application within a dispensing pad 20. While the actual concentration of the surface active agent (surfactant) is not critical, excellent results were obtained where an anionic type surfactant such as a sulphonated alkyl diphenyl oxide, available under the tradename Dowfax, was used in approximately 2 percent by weight concentration.

It will, of course, be further understood by those skilled in the chemical arts that various other minor ingredients may be added to the above solution without significantly altering its utility in the present application. These non-critical additional ingredients may include additional surface active agents, water miscible organic solvents and germicidal agents, etc.

The application of the solution of the first chemical such as ferric chloride is best accomplished by rolling or pressing the person's fingers on the surface of a dispensing pad 20 containing a rigid porous plate 22. In this regard it is to be noted that in order to obtain an acceptable fingerprint the correct amount of solution must be applied to the fingers. Application of an insufficient amount of solution ultimately results in a weak, illegible fingerprint. Application of unduly large quantities of solution results in wetting the valley areas between the fingerprint ridges and ultimately causes a smudged or smeared fingerprint.

The rigid porous plate 22 used in the novel process of the present invention is preferably of a ceramic material. In the event it is soaked with the solution of the first chemical it may act as a reservoir of that chemical. In this case, the use of a relatively thick ceramic plate provides an advantage since a relatively large quantity of the solution can be stored therein. In this type of an application a ceramic plate of approximately one quarter to one inch thickness is preferred.

Figure 4:
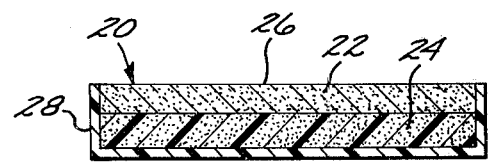
FIG. 4 is a cross sectional view of a preferred embodiment of a dispensing pad of the present invention.

Alternatively, and perhaps more advantageously the ceramic plate is approximately one quarter of an inch in thickness and is positioned to lie flatly juxtaposed to and in contact with a reservoir 24 of the solution of the first chemical, shown in FIG. 4. The reservoir 24 comprises a resilient foam or spongy or like material having interconnected interstitial spaces wherein the volume of the void within the structure is relatively large. A preferred reservoir 24 for application in the present invention is made from a silicone rubber foam pad having a large volume of interstitial spaces. Alternatively the preferred reservoir 24 comprises a felt pad.

The reservoir 24 is soaked or saturated with the solution of the first chemical. As the rigid, porous ceramic plate 22 is in intimate contact therewith, the solution, due to capillary action, rises through the ceramic plate to its surface 26. On the surface 26 it is available for delivery to the fingers of a person.

In order to have the correct amount of solution available for delivery on the surface 26 the thickness of the ceramic plate 22 and particularly its pore size is critical. A ceramic plate 22 of approximately $\frac{1}{4}$ of an inch thickness and having an average pore size in the range of 4.50–5.50 microns has been found to provide excellent results. Pore sizes significantly below the 2.00 micron range are incapable of delivering a sufficient amount of solution at the surface 26. Pore sizes significantly above 8.00 microns appear to deliver an excess amount of solution which ultimately results in a smudged or smeared fingerprint.

However, a ceramic plate 22 having the correct pore size results in a delivery of the requisite, correct amount of the solution to the fingers substantially independently from the pressure exerted by the fingers upon the ceramic plate 22. Thus the amount of solution to be applied is objectively determined and a high quality resulting fingerprint image is assured.

The use of the rigid porous plate 22 provides an additional advantage by eliminating or greatly reducing the possibility of a relative slip between a finger pressed on the plate 22 and the liquid film of the chemical present thereon. The absence of the slip further provides for obtaining a high quality fingerprint image.

The rigid, porous plate 22 together with the foamy or spongy reservoir 24 is conveniently housed in a plastic or like tray 28 of a complementary size. It is to be noted that while the preferred material for the ceramic plate 22 is unglazed porcelain, a rigid porous plate manufactured from other materials such as for example sintered plastic or sintered glass material may also be suitable for application in the present invention.

In a second step of the novel method of the present invention shown in FIG. 2 the fingers wetted with the solution of the first chemical reagent are gently rolled or pressed upon a recording sheet or form 30. The recording sheet or form 30 usually comprises an absorbent fibrous material such as paper. A standard form, schematically shown in FIG. 6, designed by the Federal Bureau of Investigation of the United States (FBI), for the purpose of recording all 10 fingerprints of a person is particularly suitable for this application. Such a form is widely utilized by law enforcement and like agencies. It has some printed matter on its surface and also has predetermined locations into which the fingerprints of the thumb, index, middle and other fingers of both hands are to be deposited.

A significant advantage provided by the method and apparatus of the present invention is that the dispensing pad 20 is dimensioned in such a manner that four fingers of one hand of a person can be simultaneously wetted with the solution of the first chemical reagent. The process of simultaneously recording of the prints of four fingers of one hand is widely practiced in the fingerprinting arts. The resulting prints of 4 fingers of one hand which are obtained by just pressing without rolling of the fingers, are commonly termed "flats" or "flat prints."

Thus the gentle rolling or pressing of the fingers individually or in combination upon the recording sheet 30 deposits the solution of the first chemical reagent thereon in a pattern corresponding to the fingerprint patterns. Since the first chemical is selected to be colorless or only slightly colored, the resulting fingerprints on the recording sheet 30 are invisible or only slightly visible.

Figure 5:
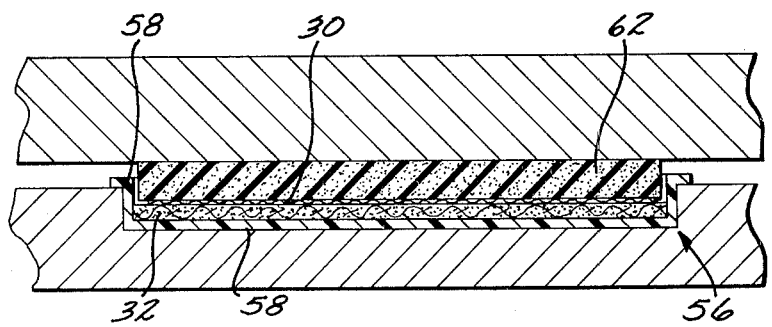
FIG. 5 is a partial cross sectional view of the preferred embodiment of a device of the present invention and a representation of the third step of the method of the present invention.

In a third step of the novel method of the present invention shown in FIGS. 3 and 5, the invisible fingerprints are developed by exposure to sublimed vapors of the second chemical. As mentioned above, the second chemical is selected to react with the first chemical to produce a highly colored substance which is to have good adherence characteristics to the surface and to the fibrous structure of the recording sheet. In addition, the second chemical to be used in the present invention must be a solid at the temperature at which the method of the present invention is practiced. The solid must have a sufficiently high vapor pressure at this temperature in order to sublime to a significant extent and therefore provide a sufficiently high concentration of the vapor phase of the second chemical for rapid reaction with the first chemical.

Providing the second chemical in a solid and in a sublimed gas phase eliminates the need for spraying the recording sheet 30 with a solution of a second chemical. Thus all the attendant disadvantages of spraying are eliminated. Furthermore the gaseous phase of the second chemical reagent is ideally suited to penetrate into the fibrous structure of the recording sheet 30 and to react therein with the first chemical reagent. The resulting fingerprints, since they are not only adhered to the surface of the recording sheet, but are also contained within the fibrous structure thereof, are substantially indelible.

8-hydroxyquinoline having a melting point at 75°–76° and the requisite, high vapor pressure at room temperature is ideally suited for application in this third step of the novel method of the present invention. The chemical reaction which occurs between ferric chloride and 8-hydroxyquinoline to produce a dark blue, almost black chelate compound is described by the following chemical equation:

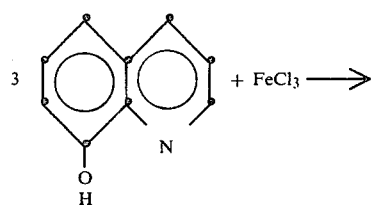

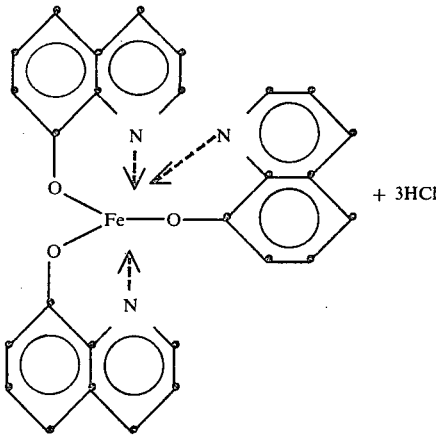

where the dotted arrows in the structure indicate chelate type bonding of the lone electron pair of each nitrogen to the vacant orbitals of the iron atom.

Development of the recording sheet 30 having the invisible fingerprints thereon is best accomplished in the practice of the present invention by positioning the recording sheet 30 in intimate contact with an at least slightly resilient pad 32 shown in FIGS. 3 and 5 containing a solid form of 8-hydroxyquinoline. This is done by simply laying the recording sheet upon the resilient pad 32 with the side having the invisible fingerprint thereon facing downward. Optionally slight pressure may be exerted upon the recording sheet 30 to assure optimal contact with the resilient pad 32.

The resilient pad 32 has a fibrous or open porous structure which contains the 8-hydroxyquinoline within its interstitial spaces. In practice a simple blotter paper having approximately 1/32 of an inch thickness or a felt pad having approximately 1/16 of an inch thickness have been found to be ideally suitable for this application.

The blotter paper or the felt pad having 8-hydroxyquinoline crystals within its structure is readily prepared by simply soaking it with a highly concentrated solution of 8-hydroxyquinoline dissolved in a volatile organic solvent. A saturated solution of 8-hydroxyquinoline in acetone obtained at room temperature is preferred for this purpose. However, other organic solvents, such as for example ethyl alcohol may also be advantageously used. After the blotter paper or the felt pad has been soaked in the solution of 8-hydroxyquinoline, it is removed therefrom and dried until the solvent evaporates. The evaporated solvent leaves behind finely dispersed crystals of 8-hydroxyquinoline within the fibrous structure of the blotter paper or the felt pad.

Figure 6:
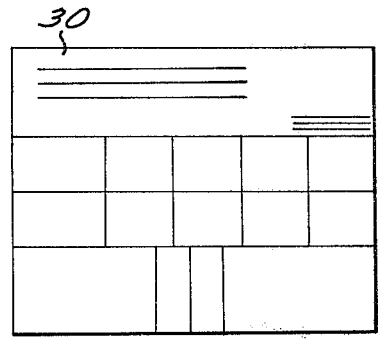
FIG. 6 is a schematic representation of a recording sheet.

Exposure of the recording sheet 30 to a gaseous phase of 8-hydroxyquinoline emanating from the blotter paper requires only a few minutes for satisfactory development of the fingerprints. The schematic drawing of FIG. 6 shows the recording sheet. At the time of removal of the recording sheet 30 from exposure to the gaseous phase of 8-hydroxyquinoline, the developed fingerprints are of a completely satisfactory intensity. Nevertheless since some 8-hydroxyquinoline is absorbed on the surface and within the fibrous structure of the recording sheet, the chemical reaction between 8-hydroxyquinoline and ferric chloride is not completely arrested by removal of the recording sheet from the blotter paper. Consequently, a further darkening of the fingerprint images still occurs for a period of time.

It is to be noted in this regard that the chemical reagent pair of 8-hydroxyquinoline and ferric chloride is ideally suited for an application in the novel method of the present invention. However other chemical reagent pairs may become apparent to those skilled in the art in light of the teachings of the generic principles of the present invention. Particularly other metal salts, the cationic component of which is capable of yielding a colored chelate compound with 8-hydroxyquinoline, such as for example vanadium salts may be used in the present invention.

Furthermore, bringing the recording sheet having the latent fingerprints thereon into intimate contact with a substantially resilient pad containing 8-hydroxyquinoline crystals within its structure is also ideally suited for the development step of the novel process of the present invention. Nevertheless other means to expose the invisible fingerprints to the vapors of 8-hydroxyquinoline or like chemical may be substituted in this particular step of the process. Additionally, the sublimation of 8-hydroxyquinoline or like chemical may be facilitated by application of a slight amount of heat. Consequently the above deviations from the preferred process described here in detail merely comprise alternative embodiments of the same and are therefore within the scope thereof.

Referring to FIGS. 1 through 3 a preferred embodiment of the device of the present invention is disclosed. The compact apparatus or device 34 is highly suitable for expeditious performance of the novel steps of the present invention. The device 34 comprises an upper plate or platen 36 and a lower plate or platen 38. The lower platen 38 is mounted upon suitable legs 39 which support the entire device 34. Both plates or platens are substantially rectangular in shape and are of substantially equal lengths and width in relation to one another. The two platens 36 and 38 are connected by a hinged structure 40 on a shorter side 42 of each plate or platen. The hinge 40 thus allows the pivotal motion of the upper platen 36 relative to the lower platen 38. The platens may comprise wood, simulated wood, suitable metal or plastic material.

A bar 44 having a substantially rectangular cross section and a length substantially co-equal with the length of a shorter side 42 of the plates or platens is secured between the two platens 36 and 38 to the lower platen 38. The bar 44 is mounted substantially adjacent to the hinged structure 40 and is dimensioned in such a manner that in a closed position, shown in FIGS. 1 and 2, the two platens 36 and 38 are disposed substantially parallel to one another. In alternative embodiments of the device of the present invention the bar 44 may be unitarily constructed with the lower platen 38.

Referring to FIGS. 1 and 2 the mounting of the plastic or like tray 28 containing the ferric chloride dispensing pad 20 within the upper platen 36 is disclosed. An indentation or offset portion (not shown) dimensioned to receive the substantially rectangular plastic tray 28 is provided within the upper platen 36. The indentation or offset portion extends to an edge of the upper platen 36 on its longer side 46 so that the plastic tray 28 can be conveniently slid into the indentation or offset portion. When properly inserted the dispensing pad 20 lies substantially flush with the upper surface 48 of the upper platen 36 and is held therein by friction.

A pad cover 50 made from metal or other suitable material such as plastic is provided to secure the dispensing pad 20 in its place. The pad cover 50 is secured to the upper surface 48 of the upper platen 36 by a suitable hinge (not shown) and is therefore simply folded up for the insertion of the dispensing pad 20. An orthogonal portion 51 of the pad cover 50 is designed to cover an edge along the longer side 46 of the upper platen 38 in the area where the offset portion or indentation is located. Therefore when the pad cover 50 occupies a folded down position the plastic tray 28 holding the dispensing pad 20 is entirely hidden from view and is protected from contamination from the environment.

A rectangular bracket or card holder 52 larger in size than the pad cover 50 is provided proximate to the same longer side 46 of the upper platen 36 as the pad cover 50. The bracket 52 is also attached by a hinge (not shown) to the upper surface 48 of the upper platen 36. One side 54 of the bracket 52 is bent in a plane substantially perpendicular to the plane generally defined by the bracket 52 and is therefore disposed substantially parallel to the longer edge 46 of the upper platen 36. The bracket or card holder 52 is hinged to the upper surface 48 on a side which is parallel with the bent side 54. All the three remaining sides, except for the bent side 54, are dimensioned to lie substantially flush with the upper surface 48 when the bracket 52 is in a folded down position.

The purpose of the bracket 52 is to temporarily secure and hold steady a fingerprinting card of a predetermined size such as the standard FBI fingerprinting card. This fingerprinting card which comprises the recording sheet 30, is thus held secure for the second step of the process of the present invention, i.e. for the deposition of the invisible fingerprints on the recording sheet 30.

Referring to FIG. 3 the apparatus or device 34 of the present invention is shown with the platens 36 and 38 being disposed in an open position. The lower platen 38 contains a substantially, centrally located indentation or trough 56. The latter is best seen on the cross sectional view of FIG. 5. A tray 58 built from plastic or other suitable material which is dimensioned to fit within the trough 56 is inserted into the trough 56.

The tray 58 is adapted to receive the resilient pad 32, which in the preferred embodiment comprises a blotter paper or a felt pad containing the second chemical 8-hydroxyquinoline. The dimensions of the trough 56, tray 58 and blotter paper 32 are such that the recording sheet 30 is readily laid upon the surface of the blotter paper 32. It may be substantially confined against lateral movement by the vertically disposed walls 60 of the tray 58.

A resilient foam cushion 62 adapted to interface with the resilient pad 32 and with the recording sheet 30 when the latter is laid upon the resilient pad 32 for development of the latent fingerprints, is secured to the upper platen 36. As the recording sheet 30 is laid upon the resilient pad 32 for development and the upper platen 36 of the device 34 is closed, the foam cushion 62 exerts slight pressure upon the recording sheet 30. The slight pressure assures intimate contact between the recording sheet 30 and the resilient pad 32. Furthermore, when the upper platen 36 of the device 34 is in a closed position, the foam cushion 62 which is dimensioned to fit tightly within the tray 58 acts as a seal. The seal prevents an undesirable loss of the second chemical reagent by sublimation into the atmosphere.

In order to further insure intimate contact between the recording sheet 30 and the resilient pad 32 a latching mechanism 64 is provided on one side of the apparatus or device 34. Such latching mechanisms are well known in the prior art and therefore need not be described here in detail. When the upper 36 and lower platens 38 are secured to each other by the latching mechanism 64 a predetermined amount of pressure is exerted by the foam cushion 62 upon the recording sheet 30 during the process of development of the invisible fingerprints. The locked latching mechanism 64 also serves to assure substantial sealing of the apparatus or device 34 when not in use whereby an undesirable loss of the sublimable second chemical reagent into the atmosphere is prevented.

The attendant advantages of the device described here will be readily appreciated by those skilled in the art. These include the ability to supply and replace the requisite chemicals in an easy to handle, non-liquid form. For example when the supply of the first chemical reagent such as ferric chloride is exhausted, a replacement plastic tray 28 containing a new dispensing pad 20 and a new reservoir of ferric chloride 24 can be simply inserted in the indentation provided in the upper platen 36. When the second chemical reagent such as the 8-hydroxyquinoline is exhausted, the resilient pad 32, blotter paper or felt pad containing the same merely needs to be discarded and a new one inserted into the tray 58. Furthermore the dimensions of the dispensing pad 20 enable the operator of the device 34 to wet at his option 4 fingers of the person to be fingerprinted with the solution of the first chemical. The recording sheet 30 is held steady for the deposition of the invisible fingerprints. The recording sheet 30 containing up to 10 individual fingerprints plus "flat prints" of both hands is developed in one single quick step. Finally human exposure to toxic chemicals is minimized and the possibility of staining the fingers with highly colored chemicals is entirely eliminated.

What has been described above is a novel method of inkless fingerprinting and a novel device particularly adapted for performing the method. It will be readily apparent to those skilled in the art that various modifications of both the method and the device of the present invention are possible within the generic principles disclosed by this invention and accordingly the scope of the present invention should be interpreted solely from the following claims.

What is claimed is:

1. An apparatus for recording fingerprints of a person, the apparatus comprising:
   first means for applying a solution of a first chemical to at least one fingerprint pattern area of a person;
   a recording surface onto which the solution of the first chemical is deposited in substantial conformity with the fingerprint pattern, and
   second means for containing a second chemical and for exposing the recording surface having the deposited solution of the first chemical thereon to a gaseous phase of the second chemical,
   the second chemical having a melting point above the operating temperature of the apparatus and sufficient vapor pressure to cause significant sublimation of the second chemical, the gaseous phase of the second chemical capable of reacting with the first chemical to yield a colored reaction product whereby the fingerprint pattern of the person is developed on the recording surface and is recorded.

2. The apparatus of claim 1 wherein the first means comprise a substantially rigid, porous member capable of dispensing a film of the solution of the first chemical upon at least one finger of the person.

3. The apparatus of claim 2 wherein the porous member is connected to a reservoir of the first chemical, the reservoir comprising a resilient pad containing the solution of the first chemical within the integral structure thereof, the pad being in intimate contact with the porous member.

4. The apparatus of claim 2 wherein the solution of the first chemical is a substantially aqueous solution and wherein the first chemical is a metal salt the cationic component of which is capable of reacting with the second chemical to yield the colored reaction product.

5. The apparatus of claim 4 wherein the first chemical is a water soluble salt of ferric ions and the second chemical is 8-hydroxyquinoline.

6. The apparatus of claim 5 wherein the solution contains 5–40% ferric chloride.

7. The apparatus of claim 1 wherein the second means comprise a member containing interstitial spaces within the structure thereof and mechanical means for maintaining intimate contact between the recording surface and the member, the member containing dispersed within the structure thereof a solid phase of the second chemical.

8. The apparatus of claim 7 wherein the second chemical is 8-hydroxyquinoline.

9. The apparatus of claim 8 wherein the member is a fibrous member and the first chemical is ferric chloride.

10. The apparatus of claim 1 adapted for simultaneous recording of a plurality of fingerprints of one hand of the person.

11. An apparatus adapted for recording a plurality of fingerprints of one hand of a person, the apparatus comprising:
    a lower and an upper structural member connected by a hinge for pivoting movement in relation to one another;
    a substantially rigid dispensing member in intimate contact with a reservoir member having one of a porous and fibrous structure, the dispensing and the reservoir member being mounted to the upper structural member, the reservoir member containing a substantially aqueous solution of a metal salt whereby the dispensing member is capable of depositing a film of the solution upon the fingers of a person;
    a recording sheet;
    mechanical means provided in the upper structural member for temporarily but fixedly positioning the recording sheet to enable the person to roll his fingers in predetermined locations upon the recording sheet, and
    a member mounted within one of the upper and the lower structural members and adapted for disposition in close proximity to the recording sheet, the member containing a solid phase of an organic chemical, the organic chemical capable of reacting with the metal salt to form a colored substance capable of substantially adhering to the recording sheet, the organic chemical having a vapor pressure sufficient to result in sublimation of the second chemical to a significant extent whereby sublimed vapors of the second chemical react with the metal salt to provide visible recorded fingerprints of the person.

12. The apparatus of claim 11 further comprising a latching mechanism to lock the upper and lower structural members in a substantially parallel position in relation to one another.

13. The apparatus of claim 11 wherein the dispensing member is a porous ceramic member having an average pore size of 2.0–8.0 microns.

14. The apparatus of claim 13 wherein the average pore size is 4.0–6.0 microns.

15. The apparatus of claim 11 wherein the member adapted to interface with the recording sheet is a member having interstitial spaces and containing therein the organic chemical 8-hydroxyquinoline.

16. The apparatus of claim 15 wherein the dispensing member is a porous ceramic member having an average pore size of 2.0–8.0 microns and the metal salt is a ferric salt.

17. The apparatus of claim 16 wherein the ferric salt is ferric chloride and the substantially aqueous solution contains 5–40% ferric chloride.

18. An apparatus for recording at least one fingerprint of a person upon a recording sheet, the apparatus comprising the combination of:

first means for applying a solution of a first chemical to at least one fingerprint pattern area of a person wherefrom the solution of the first chemical is deposited on the recording sheet in substantial conformity with the fingerprint pattern, and second means for exposing in a predetermined temperature range the recording sheet having the deposited solution of the first chemical thereon to a sublimed gaseous phase of a second chemical, the second chemical being a solid in the predetermined temperature range and having sufficient vapor pressure to result in significant sublimation of the second chemical, the gaseous phase of the second chemical capable of reacting with the first chemical to yield a colored reaction product whereby the fingerprint pattern of the person is developed on the recording sheet and is recorded.

19. The apparatus of claim 18 further comprising third means for causing the predetermined temperature range to be higher than ambient temperature.

* * * * *